US006575624B2

(12) United States Patent
Noegel et al.

(10) Patent No.: US 6,575,624 B2
(45) Date of Patent: Jun. 10, 2003

(54) X-RAY APPARATUS WITH NON-CONTACTING TRANSMISSION OF DATA OR ENERGY BETWEEN MECHANICALLY CONNECTED COMPONENTS

(75) Inventors: Peter Noegel, Effeltrich (DE); Andreas Schultz, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/896,679

(22) Filed: Jun. 29, 2001

(65) Prior Publication Data

US 2002/0085682 A1 Jul. 4, 2002

(30) Foreign Application Priority Data

Jun. 29, 2000 (DE) .......................... 100 31 777
Jul. 31, 2000 (DE) .......................... 100 37 294

(51) Int. Cl.[7] .............................................. H05G 1/02
(52) U.S. Cl. .......................... 378/198; 378/15; 378/196; 378/197
(58) Field of Search ............................... 378/4, 15, 19, 378/196, 197, 198

(56) References Cited

U.S. PATENT DOCUMENTS

| 4,982,415 | A |   | 1/1991  | Shibata et al. ............. 378/15 |
| 5,231,653 | A |   | 7/1993  | Pfeiler et al. ................ 378/91 |
| 5,530,424 | A |   | 6/1996  | Harrison et al. ............ 340/500 |
| 5,596,437 | A |   | 1/1997  | Heins ........................ 359/144 |
| 5,608,771 | A | * | 3/1997  | Steigerwald et al. .......... 378/15 |
| 6,065,710 | A |   | 5/2000  | Richter et al. ........... 242/388.6 |
| 6,120,180 | A | * | 9/2000  | Graumann ................. 378/206 |
| 6,139,183 | A | * | 10/2000 | Graumann ................. 378/206 |
| 6,213,638 | B1 | * | 4/2001 | Rattner ...................... 378/198 |
| 6,301,324 | B1 | * | 10/2001 | Pearson, Jr. et al. ......... 378/15 |
| 6,327,330 | B1 |   | 12/2001 | Peter ........................... 378/19 |
| 6,396,613 | B1 | * | 5/2002  | Harrison et al. ............ 359/173 |
| 6,409,381 | B1 | * | 6/2002  | Siebenhaar et al. ........ 378/197 |
| 6,501,821 | B2 | * | 12/2002 | Betz ............................ 378/15 |

* cited by examiner

Primary Examiner—Drew A. Dunn
Assistant Examiner—Allen C. Ho
(74) Attorney, Agent, or Firm—Schiff Hardin & Waite

(57) ABSTRACT

An X-ray apparatus, having a C-arm X-ray device with at least one electrically operable component that is arranged at a C-arm that is adjustable relative to a holding mechanism, has an arrangement disposed in or at the C-bend or the component and are connected to the component for the transmission of data and/or energy, and another arrangement for the transmission of energy that are disposed in or at a housing connected to the holding mechanism. The exchange of data and/or the transmission of energy between these arrangements ensues in contactless fashion, and the transmission of the data and/or of the energy ensues continuously.

35 Claims, 2 Drawing Sheets

X-RAY APPARATUS WITH NON-CONTACTING TRANSMISSION OF DATA OR ENERGY BETWEEN MECHANICALLY CONNECTED COMPONENTS

BACKGROUND OF THE INVENTION

1. Field of the Invention

The present invention is directed to an X-ray apparatus of the type having a C-arm X-ray device with at least one electrically operable component that is arranged at a C-arm that is adjustable relative to a holding mechanism.

2. Description of the Prior Art

It is conventional to arrange an X-ray source and an X-ray receiver at a C-arm of a C-arm X-ray device, which is adjustable relative to a holding mechanism for the C-arm that is connected to the housing of the C-arm X-ray device. As a rule, the X-ray apparatus also has a separately implemented viewing device unit connected to the C-arm X-ray device via at least one cable. Given such an X-ray apparatus, the energy for the operation of the X-ray source and of the X-ray receiver as well as all data to be transferred between the X-ray source, the X-ray receiver and, for example, a data processing means arranged in the viewing device unit are transmitted via cables.

A cable module as disclosed, for example, in German OS 197 43 215 is provided in the holding mechanism for the transmission of the energy via the mechanical interface via the holding mechanism and the C-arm to the electrically operable components arranged at C-arm or for the transmission of the data between the components arranged at the C-arm and electrically operable components arranged in the housing or the viewing device unit. The cable module has cables that can be wound onto and off of drums via which the X-ray source and the X-ray receiver as well as other electrically operable components, as may be arranged at the C-arm and connected to the cables, are supplied with energy and via which the data transfer ensues between the X-ray source, the X-ray receiver and, for example, the data processing means.

A disadvantage of this form of transmission of energy and data via the mechanical interface between the holding mechanism and the C-arm of the X-ray device is the structural space that the cable module occupies in a C-arm X-ray device, particularly in the holding device, as well as the comparatively large mass of the cable module, amounting to more than 52 kg.

U.S. Pat. No. 4,982,415, moreover, discloses a computed tomography apparatus with a gantry carrying an X-ray system that is rotatable around a rotational center, whereby measured data are intermediately stored in a data memory rotating together with the gantry during a scan, the measured data being transmitted in non-contacting fashion to a stationary unit of the computed tomography apparatus upon standstill of the gantry. This data transmission takes place via a data transfer unit. The transmission of the data thus cannot ensue continuously.

German OS 198 37 442 discloses a computed tomography apparatus wherein the transmission of data from a rotor carrying an X-ray source and an X-ray receiver ensues in non-contacting fashion, using transmission and reception devices, to a console that is stationary relative to the rotor.

German PS 42 07 007 discloses a computed tomography apparatus wherein the data transmission from a rotor onto a console ensues with a rotating current coupling. The current coupling comprises an annular, rotating disk with interconnects with which stationary signal pickups are in contact.

German OS 195 33 819 discloses an apparatus and a method for a communication with a high data rate in a computed tomography system wherein a coupler is secured to a stationary frame and is arranged adequately close to a transmission line secured to the rotating frame for establishing a radio coupling in order to transmit an applied, modulated signal.

Further, German OS 43 03 643 discloses an X-ray system having a number of system components each allocated to a data transmission node in the CAN protocol, the data input and data output thereof having an interactive connection to other data transmission nodes via transmitters or receivers. The transmitters and receivers of at least some data transmission nodes are fashioned for the contactless transmission of data. The contactless transmission of the data is intended to assure a faster and more dependable data transmission.

The article, "Virtuelles Kabel" by Wilfried Blaesner, Design & Elektronik, 02/99, pages 16 through 18, describes a radio data transmission system that operates according to the DECT standard.

German PS 196 46 607 discloses a method and an apparatus for the positionally correct processing of X-ray cassettes having a data memory. A sensor checks whether the data memory of a cassette is at a specific position relative to the sensor at a specific point in time.

U.S. Pat. No. 5,231,653 discloses transmitting image data from a C-arm X-ray device to a data processing means in non-contacting fashion using an optical transmission path. A disadvantage of optical transmission of data, however, is the required line-of-sight path between the transmitter and the receiver for the data, requiring a specific arrangement of the transmitter relative to the receiver.

SUMMARY OF THE INVENTION

An object of the present invention is to provide an X-ray apparatus of the type initially described wherein data transmission and/or energy transmission via the mechanical interface between the holding mechanism and the C-arm is simplified.

This object is inventively achieved in an X-ray apparatus having a C-arm X-ray device with at least one electrically operable component that is arranged at the C-arm that is adjustable relative to a holding mechanism, having a first data transmitter and a data and energy receiver arranged at the C-arm or the component. A data and energy transmitter and a data receiver are arranged at the holding mechanism or at a housing connected to the holding mechanism for the transmission of data and/or energy. The exchange of data and/or transmission of energy between these transmitters and receivers ensues contactless, and whereby the transmission of data and/or energy can ensue continuously. As used herein, disposing these items "at" the designated apparatus part encompasses disposing them "in" the designated apparatus part. Because the transmission of data and/or energy ensues in non-contacting fashion, a cable module that occupies structural space and increases the mass of the X-ray device can be foregone. Accordingly, the data transmission and/or the energy transmission via the mechanical interface between the holding mechanism and the C-arm is significantly simplified. Moreover, the transmission of data and/or energy in the present invention can ensue continuously during the adjustment of the C-arm relative to the holding mechanism, i.e., without intermediate storage of data and/or energy, which would involve additional outlay at the X-ray device.

Further, the contactless transmission of data and/or energy via the mechanical interface makes it possible to keep this as simple as possible, so that the preconditions are created for replacing or exchanging the C-arm provided with at least one component with a different C-arm in a relatively simple way without being impeded by means for the data and/or energy transmission.

The aforementioned receiver for data and/or energy and the aforementioned transmitter for data can be separate components or can be combined as a single component. If multiple components are used, the functions respectively performed by the multiple components can be distributed in a suitable manner, such as by separating transmission functions and reception functions or by separating energy-related functions and data-related functions. The same considerations apply to the transmitter for energy and/or data and the receiver for data at the holding mechanism or the housing.

In one embodiment of the invention the transmitters and receivers for the transmission of data include at least one transmission device and at least one reception device for the signal-carrying waves. According to versions of the invention, the transmission device can be an infrared transmitter and the reception device can be an infrared receiver or the transmission device can be a radio transmitter and the reception device can be a radio receiver. The employment of transmission and reception devices for signal-carrying waves for the transmission of data within the C-arm X-ray device is an especially simple possibility for the contactless transmission of data.

In an embodiment of the invention, the contactless exchange of the data and/or the transmission of energy ensues inductively, with the transmitters and receivers including at least one pair of coupled coils. Inductive coupling also represents a suitable possibility for transmitting data and/or energy via the mechanical interface between the C-arm and the holding mechanism. Whereas a coupling coil of the transmitter for the transmission of data and/or energy, and/or a coupling coil for the data receiver, is preferably arranged in the holding mechanism of the C-arm X-ray device, a coupling coil of the receiver for data and/or energy, and/or a coupling coil for the data transmitter, is preferably arranged along the C-arm. Given the adjustment of the C-arm relative to the holding mechanism, the coupling coils are moved relative to one another, whereby the coupling gap between the coupling coils is kept approximately constant during the adjustment, so that a dependable data transmission and/or energy transmission can ensue via the coupling coils.

In an embodiment of the invention the contactless transmission of energy ensues via microwaves. In a version of this embodiment, the receiver fr data and/or energy (serving as an energy receiver) has at least one component provided with a transmission medium for microwaves, and the transmitter for data and/or energy (serving as an energy transmitter) has at least one microwave generator collaborating with the component. The transmission medium, which comprises dipoles, can, for example, be water and the component can be a plastic tube filled with the water. Such a water-filled plastic tube, can be arranged at the C-arm so that, given adjustment movements of the C-arm relative to the holding mechanism, it is moved such relative to a microwave generator arranged in the holding mechanism so that the microwave generator can introduce microwaves into the transmission medium. The microwaves are ultimately transmitted via the transmission medium to one or more components connected to the plastic tube, so that the component or components can be supplied with energy via a suitable emission of the microwaves from the plastic tube.

In another embodiment of the invention the receiver for data and/or energy (serving as an energy receiver) has at least one waveguide, and the transmitter for data and/or energy (serving as an energy transmitter) has at least one microwave generator collaborating with the waveguide. In this embodiment, the microwave generator introduces microwaves into the waveguide, these being transmitted to the component or components connected to the waveguide, so that the component or components can be supplied with energy in this case as well after suitable emission of the microwaves.

In an embodiment of the invention the housing is implemented as an apparatus carriage and the electrically operable component can be an X-ray source or an X-ray receiver or a camera allocated to the X-ray receiver.

In another embodiment of the invention, the X-ray apparatus includes a second device unit that has a processor for processing data and at least one display device. In the case of an X-ray apparatus having a C-arm X-ray device, the second device unit forms what is referred to as a viewing device unit on whose display device X-ray images acquired with a C-arm X-ray device can be displayed.

In order to also avoid cabling between the X-ray device and the second device unit, the second device unit in an embodiment of the invention likewise has an arrangement for the contactless exchange of data that interact with the arrangement for contactless exchange of data of the X-ray device, particularly with the receiver for data and/or energy and the transmitter for data disposed at the C-arm or the component.

Accordingly, in an embodiment the second device unit has at least one transmission device and/or at least one reception device for signal-carrying waves. The transmission device can be an infrared transmitter and the reception device can be an infrared receiver, or the transmission device can be a radio transmitter and the reception device can be a radio receiver. In this way, data can be transmitted and/or received to/from the arrangement of the C-arm or the component directly of the X-ray device is assured, so that the data transfer between the second device and the component arranged at the C-arm need not necessarily ensue via the transmitter or receiver disposed at the holding mechanism.

DESCRIPTION OF THE PREFERRED EMBODIMENTS

Figure 1:
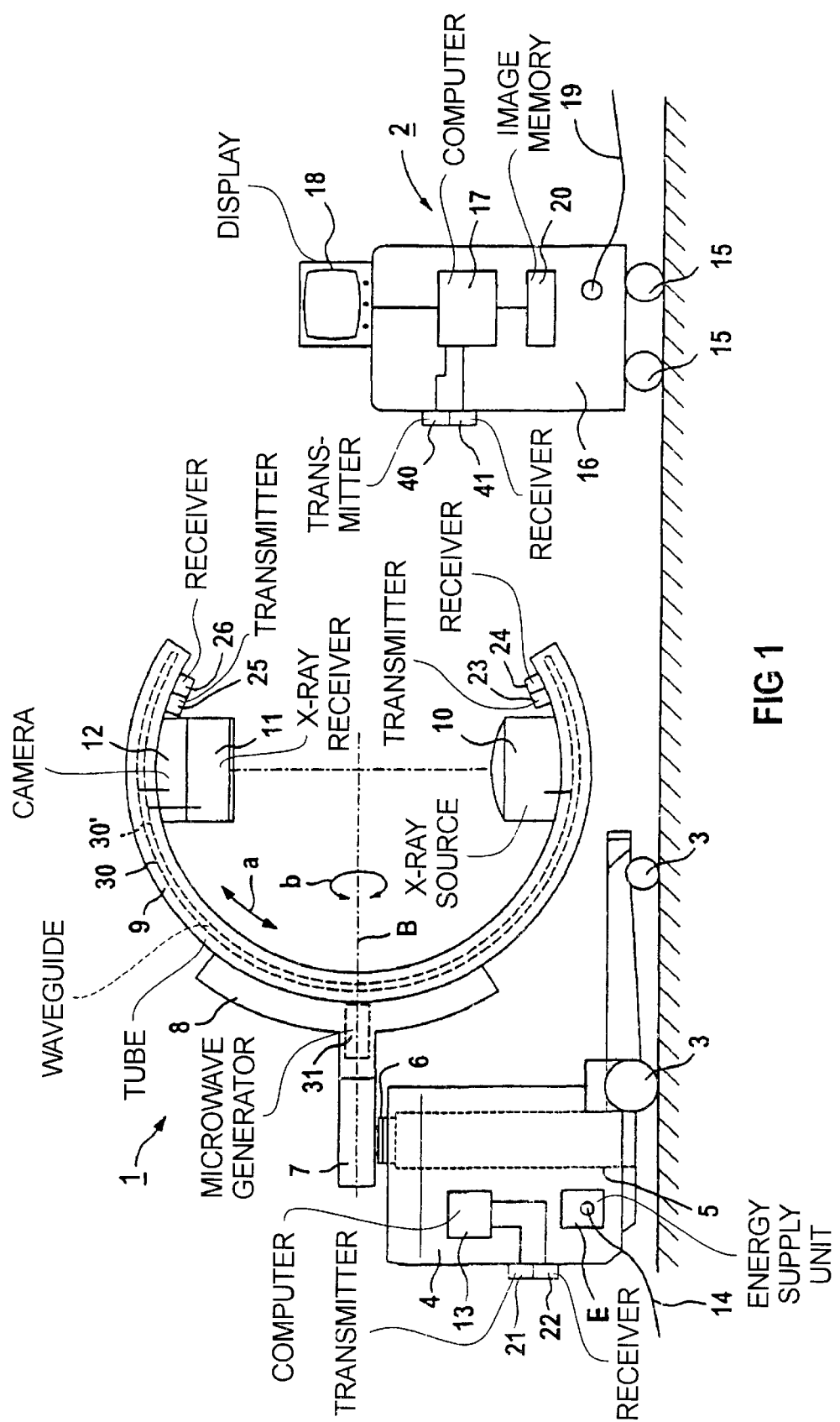
FIG. 1 is a schematic block diagram of a first embodiment of an X-ray apparatus constructed and operating in accordance with the principles of the present invention.

In an exemplary first embodiment, the inventive X-ray apparatus shown in FIG. 1 has a C-arm X-ray device 1 and a viewing device unit 2.

The C-arm X-ray device 1 has a device carriage 4 movable on wheels 3 in which a lifting mechanism 5 (only schematically indicated in FIG. 1) having a column 6 is arranged. A holder 7 to which a holding mechanism 8 for seating a C-arm 9 is arranged is secured to the column 6. Opposite one another, an X-ray radiator 10 emitting a conical X-ray beam and an X-ray receiver 11 are arranged at the C-arm 9. In the exemplary embodiment, the X-ray receiver 11 is a known X-ray image intensifier that is followed in a known way by a camera 12.

The C-arm 9 is adjustable along its circumference in the holding mechanism 8 (as indicated by the double arrow a, orbital movement). Moreover, the C-arm 9 together with the holding mechanism 8 can be pivoted around an axis B (double arrow b, angulation movement) that proceeds substantially horizontally through the holder 7, the holding mechanism 8 and the C-arm 9.

In the exemplary embodiment, the C-arm X-ray device 1 also has a processor for processing data in the form of a known computer 13. The energy supply of the C-arm X-ray device in the exemplary embodiment ensues via an energy supply cable 14 that is connectable to an energy supply source (not shown).

The viewing device unit 2 of the X-ray apparatus has a device carriage 16 movable on wheels 15, a processor for processing data in the form of a known computer 17, and a display device in the form of a monitor 18 connected to the computer 17. The viewing device unit 2 is connectable by an energy supply cable 19 to a known energy supply source that is not shown in FIG. 1.

The C-arm X-ray device 1 as well as the viewing device unit 2 each has a control console (not explicitly shown in FIG. 1) for operating the C-arm X-ray device 1 or the viewing device unit 2, respectively. The C-arm X-ray device 1 and the viewing device unit 2 collaborate during operation of the X-ray apparatus so that, for example, X-ray images acquired with the C-arm X-ray device 1 are transmitted to the viewing device unit 2. After image processing (if necessary) by the computer 17, these images are displayed on the monitor 18 and are also able to be intermediately stored in an image memory 20 of the viewing device unit 2 that is connected to the computer 17.

As initially mentioned, cables are provided in known C-arm X-ray devices for the data transfer between components arranged at the C-arm 9, for example the X-ray radiator 10, the X-ray receiver 11 and the camera 12, and components arranged in the housing 4, for example the computer 13, as well as for the energy supply of the components arranged at the C-arm 9. In particular, the cable laying is accomplished with a complex cable module via the mechanical interface between the holding mechanism 8 and the C-arm 9.

In the exemplary embodiment of the invention, the data exchange and/or the energy supply are accomplished via the mechanical interface so that the data transmission and the energy transmission can ensue without contact but nonetheless continuously, namely during the adjustment of the C-arm 9 relative to the holding mechanism 8 as well.

In the exemplary embodiment shown in FIG. 1 data transmission between the computer 13, the X-ray radiator 10, the X-ray receiver 11 and the camera 12 ensues with transmission and reception devices for signal-carrying waves. In the exemplary embodiment, a transmission device 21 connected to the computer 13 and a reception device 22 likewise connected to the computer 13 are secured to the device carriage 4 for this purpose. In the exemplary embodiment, further, a transmission device 23 and a reception device 24 are secured to the C-arm 9 in the region of the X-ray radiator 10 and a transmission device 25 and a reception device 26 for a signal-carrying waves are secured in the region of the X-ray receiver 11 and the camera 12. The transmission device 23 and the reception device 24 are connected (in a way not shown) to the X-ray radiator 10, and the transmission device 25 and the reception device 26 are connected (in a way that is not shown) to te X-ray receiver 11 and the camera 12. Using the transmission and reception devices, accordingly, it is possible to transmit data in non-contacting fashion and continuously from the computer 13 to the X-ray radiator 10, to the X-ray receiver 11 as well as to the camera 12 as well as in the opposite direction. Moreover, it can also be adequate to arrange only one transmission device and only one reception device for the data transfer at the C-bend 9 and to connect the X-ray radiator 10 as well as the X-ray receiver 11 and the camera 12 thereto, so that a bidirectional data transfer is possible. The transmission and reception devices can be known infrared transmitters and infrared receivers or known radio transmitters and radio receivers.

The energy transmission to the X-ray radiator 10, to the X-ray receiver 11 and to the camera 12 via the mechanical interface between the holding mechanism 8 and the C-arm 9 ensues in non-contacting fashion with microwaves in the exemplary embodiment shown in FIG. 1. In this exemplary embodiment, a component filled with a transmission medium for microwaves, which must be a transmission medium having a dipole, is secured for this purpose in the inside of the C-arm 9. This component is adjusted relative to the holding mechanism 8 together with the C-arm 9. The component is conducted along the circumference of the C-arm 9. The component is preferably an arcuate plastic tube 30 that, in the exemplary embodiment, is filled with water as the transmission medium. A known microwave generator 31 is arranged in the holding mechanism 8 at a defined distance from the plastic tube 30, the microwave generator 31 being connected (in a way not shown) with a cable to an energy supply unit E of the C-arm X-ray device 1 that is connected to the energy supply cable 14. In a know way, the cable is thereby conducted via the lifting mechanism 5 and the holder 7 to the microwave generator 31 arranged in the holding mechanism 8. During operation of the C-arm X-ray device 1, the microwave generator 31 couples microwaves into the water-filled plastic tube 30, these being in turn coupled out from the plastic tube 30 at the side of the X-ray radiator 10 as well as at the X-ray receiver 11 and the camera 12. The energy that is coupled out is ultimately employed as the energy supply for the X-ray radiator 10, the X-ray receiver 11 and the camera 12.

As an alternative to the water-filled plastic tube 30, a waveguide 30' can be utilized for the transmission of the microwaves. This alternative solution is indicated in FIG. 1 by the reference character 30' in hatched form for the waveguide. The waveguide 30' interacts with the microwave generator 31 in a way comparable to the plastic tube 30.

By employing transmission and reception devices for the data transmission and by employing microwaves for the energy transmission, data and energy can thus be transmitted in non-contacting fashion in this way but nonetheless continuously via the mechanical interface between the holding mechanism 8 and the C-arm 9.

In the exemplary embodiment, the viewing device unit 2 also has a transmission device 40 and a reception device 41 for signal-carrying waves that are connected to the computer 17. The transmission and reception devices 40 and 41 are implemented equivalent to the transmission and reception devices of the C-arm X-ray device 1, i.e., either as an infrared transmitter and an infrared receiver or a radio transmitter and a radio receiver. In this way, contactless data transfer is also enabled between the computer 17 of the viewing device unit 2 and the computer 13 of C-arm X-ray device 1 as well as between the computer 17 of the viewing device 2 and the X-ray radiator 10, the X-ray receiver 11 and the camera 12. This contactless data transfer is preferably employed for the transmission of image signals generated with the camera 12 to the viewing device unit 2, on whose monitor 18 the X-ray image is acquired with the C-arm X-ray device 1 can be displayed. However, other data, for example control data, can also be transmitted from the computer 13 or the computer 17 to the components of the C-arm X-ray device 1 operated at the C-arm 9.

Figure 2:
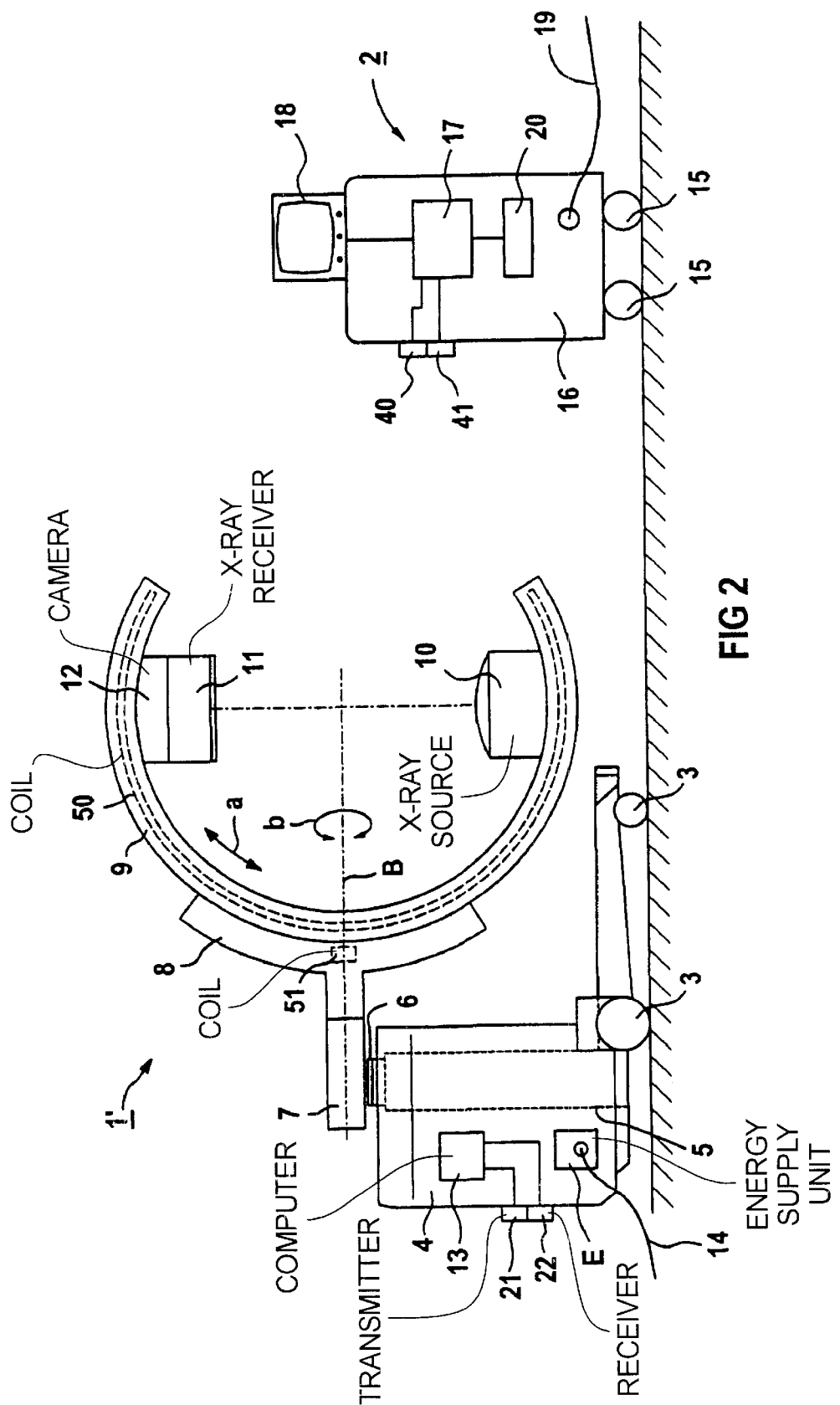
FIG. 2 is a schematic block diagram of a second embodiment of an X-ray apparatus constructed and operating in accordance with the principles of the present invention.

FIG. 2 shows a second exemplary embodiment of an inventive X-ray apparatus having a C-arm X-ray device 1' and the viewing device unit 2 from FIG. 1. Components of the C-arm X-ray device 1' that are at least essentially structurally and functionally the same as components of the C-arm X-ray device 1 of FIG. 1 are provided with the same reference characters. The C-arm X-ray device 1' shown in FIG. 2 differs from the C-arm X-ray device 1 shown in FIG. 1 in that the data and energy transmission via the mechanical interface between the holding mechanism 8 and the C-arm 9 ensues inductively. In the exemplary embodiment of FIG. 2, an arcuately implemented coupling coil 50 that has a number of turns is guided for this purpose in the inside of the C-arm 9 along the circumference of the C-arm 9. This coupling coil 50 is adjusted relative to the holding mechanism 8 together with the C-arm 9. A second coupling coil 51 is arranged in the holding mechanism 8 at a defined distance from the coupling coil 50. The second coupling coil 51 is connected (in a known way that is not shown) to the energy supply unit E of the C-arm X-ray device 1' and to the computer 13 via cables conducted via the lifting mechanism 5 and the holder 7. Coupling coils are arranged (in a way that is not shown) in the region of the X-ray radiator 10 as well as in the region of the X-ray receiver 11 and the region of the camera 12, these coupling coils being respectively electrically connected to the X-ray radiator 10 or, respectively, to the X-ray receiver 11 and to the camera 12. The coupling coils 50, 51 make it possible to transit data as well as energy continuously and in non-contacting manner via the mechanical interface between the holding mechanism 8 and the C-arm 9, so that a data transfer can ensue continuously and in non-contacting fashion between the computer 13, the X-ray radiator 10, the X-ray receiver 11 and the camera 12, and an energy supply can ensue in non-contacting fashion and continuously for the X-ray radiator 10, the X-ray receiver 11 and the camera 12. A number of coupling coils can be provided for the transmission of data and the transmission of energy, i.e. at least one further coupling coil corresponding to the coupling coil 50 can be arranged in the C-arm 9 and at least one further coupling coil corresponding to the coupling coil 51 can be arranged in the holding mechanism 8, whereby the one pair of coupling coils can be provided for the data transmission and the other pair of coupling coils can be provided for the energy transmission. However, a number of data transmission paths as well as a number of energy transmission paths can also be present, each respectively employing one pair of coupling coils.

As in the exemplary embodiment described in FIG. 1, a contactless data transfer between the C-arm X-ray device 1' and the viewing device unit 2 ensues via the transmission and reception device 21, 22 and via the transmission and reception device 40,41.

Differing from the exemplary embodiment shown in FIG. 1, the transmission and reception devices 23 through 26 need not necessarily be arranged at the C-arm 9 but can be arranged at the X-ray radiator 10, the X-ray receiver 11 or the camera 12. The transmission device 21 and the reception device 22 alternatively can be attached elsewhere, for example at the holder 7.

Further, the plastic tube 30 or the waveguide 30' need not necessarily be arranged in the C-arm 9, and the microwave generator 31 need not necessarily be arranged in the holding mechanism 8. The plastic tube 30 or the waveguide 30' alternatively can be arranged outside the C-arm 9, and the microwave generator 31 can be arranged outside the holding mechanism 8. This is also true for the coupling coils 50, 51 of the C-arm X-ray device 1'.

Further, any and all mixed forms of the exemplary embodiments shown in FIGS. 1 and 2 are conceivable. Thus, the energy transmission in the case of the exemplary embodiment shown in FIG. 1 need not necessarily ensue via microwaves but could, for example, also ensue inductively. In the case of the second exemplary embodiment, further, the data transmission as well as the energy transmission need not necessarily ensue inductively via the mechanical interface.

Moreover, an inventive X-ray apparatus need not simultaneously have both an arrangement for contactless transmission of data as well as an arrangement for contactless transmission of energy. Only an arrangement for contactless transmission of data or only an arrangement for contactless transmission of energy can be provided.

In addition to the X-ray radiator 10, the X-ray receiver 11 and the camera 12, other electrically described [sic] components can also be arranged at the C-arm and can be supplied with energy in the described way or exchange data with other electrically operated devices that are not arranged at the C-arm.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray apparatus comprising:
   a C-arm X-ray device having a C-arm and a holding mechanism, said C-arm being mechanically connected to said holding mechanism for adjustment relative to said holding mechanism;
   a housing in which said holding mechanism is disposed;
   at least one electrically operable component mounted at said C-arm, said C-arm and said at least one electrically operable component being apparatus components;
   at least one first component selected from the group consisting of a receiver for non-contacting reception of at least one of data and energy, and a transmitter for non-contacting transmission of data, mounted at at least one of said apparatus components;
   at least one second component, selected from the group consisting of a non-contacting transmitter for at least one of data and energy, and a receiver for flop-contacting receiving data, mounted at at least one of said holding mechanism and said housing, for continuously exchanging at least one of data and energy with said first component without contact with said first component; and
   a viewing device unit, separate from said C-arm X-ray device, comprising a processor for processing data produced by said at feast one electrically operating device, and a display device for displaying a result of processing of said data, said processor communicating with said first component to at least receive said data therefrom.

2. An X-ray apparatus as claimed in claim 1 wherein said processor communicates exclusively and directly with said first component to at least receive said data therefrom.

3. An X-ray apparatus as claimed in claim 2 wherein said first component comprises a transmitter for signal-carrying waves, and wherein said viewing device unit comprises a receiver for signal-carrying waves.

4. An X-ray apparatus as claimed in claim 3 wherein said transmitter for signal-carrying waves is an infrared transmitter and wherein said receiver for signal-carrying waves is an infrared receiver.

5. An X-ray apparatus as claimed in claim 3 wherein said transmitter for signal-carrying waves is an radio transmitter and wherein said receiver for signal-carrying waves is an radio receiver.

6. An X-ray apparatus as claimed in claim 2 wherein said first component comprises a transmitter for signal-carrying waves and a receiver for signal-carrying waves, and wherein said viewing device unit comprises a receiver for signal-carrying waves interacting with said transmitter for signal-carrying waves at said apparatus component, and a transmitter for signal-carrying waves interacting with said receiver for signal-carrying waves at said apparatus component.

7. An X-ray apparatus as claimed in claim 6 wherein each of said signal transmitters for signal-carrying waves is an infrared transmitter and wherein each of said receivers for signal-carrying waves is an infrared receiver.

8. An X-ray apparatus as claimed in claim 6 wherein each of said signal transmitters for signal-carrying waves is an radio transmitter and wherein each of said receivers for signal-carrying waves is an radio receiver.

9. An X-ray apparatus as claimed in claim 1 wherein said housing comprises a cart for said C-arm X-ray device.

10. An X-ray apparatus as claimed in claim 1 further comprising a viewing device unit, separate from said C-arm X-ray device, comprising a processor for processing data produced by said at least one electrically operating device, and a display device for displaying a result of processing of said data, said processor communicating with said first component to at least receive said data therefrom.

11. An X-ray apparatus comprising:
a C-arm X-ray device having a C-arm and a holding mechanism, said C-arm being mechanically connected to said holding mechanism for adjustment relative to said holding mechanism;
a housing at which said holding mechanism is disposed;
at least one electrically operable component mounted at said C-arm, said C-arm and said at least one electrically operable component being apparatus components;
at least one receiver for signal-carrying infrared waves for non-contacting reception of data, mounted at at least one of said apparatus components; and
at least one transmitter for signal-carrying infrared waves for non-contacting transmission data, mounted at at least one of said holding mechanism and said housing, for continuously exchanging data with said receiver without contact with said receiver.

12. An X-ray apparatus as claimed in claim 1 wherein said housing comprises a cart for said C-arm X-ray device.

13. An X-ray apparatus as claimed in claim 1 wherein said at least one electrically operating component is selected from the group consisting of X-ray sources, X-ray receivers, and cameras.

14. An X-ray apparatus comprising:
a C-arm X-ray device having a C-arm and a holding mechanism, said C-arm being mechanically connected to said holding mechanism for adjustment relative to said holding mechanism;
a housing at which paid holding mechanism is disposed;
at least one electrically operable component mounted at said C-arm, said C-arm and said at least one electrically operable component being apparatus components;
at least one transmitter for signal-carrying infrared waves for non-contacting transmission of data, mounted at at least one of said apparatus components; and
at least one receiver for signal-carrying infrared waves for non-contacting reception of data, mounted at at least one of said holding mechanism and said housing, for continuously exchanging data said transmitter without contact with said transmitter.

15. An X-ray apparatus as claimed in claim 14 wherein said housing comprises a cart for said C-arm X-ray device.

16. An X-ray apparatus as claimed in claim 14 further comprising a viewing device unit, separate from said C-arm X-ray device, comprising a processor for processing data produced by said at least one electrically operating device, and a display device for displaying a result of processing of said data, said processor communicating with said first component to at least receive said data therefrom.

17. An X-ray apparatus comprising:
a C-arm X-ray device having a C-arm and a holding mechanism, said C-arm being mechanically connected to said holding mechanism for adjustment relative to said holding mechanism;
a housing at which arid holding mechanism is disposed;
at least one electrically operable component mounted at said C-arm, said C-arm and said at least one electrically operable component being apparatus components;
at least one receiver for signal carrying radio waves for non-contacting reception of data, mounted at at least one of said apparatus components; and
at least one transmitter for signal carrying radio waves for non-contacting transmission of data mounted at at least one of said holding mechanism and said housing, for continuously exchanging data with said receiver without contact with said receiver.

18. An X-ray apparatus as claimed in claim 17 wherein said housing comprises a cart for said C-arm X-ray device.

19. An X-ray apparatus as claimed in claim 17 further comprising a viewing device unit, separate from paid C-arm X-ray device, comprising a processor for processing data produced by said at least one electrically operating device, and a display device for displaying a result of processing of said data, said processor communicating with said first component to at least receive said data therefrom.

20. An X-ray apparatus comprising:
a C-arm X-ray device having a C-arm and a holding mechanism, said C-arm being mechanically connected to said holding mechanism far adjustment relative to said holding mechanism;
a housing at which said holding mechanism is disposed;
at least one electrically operable component mounted at said C-arm, said C-arm and said at least one electrically operable component being apparatus components;
at least one transmitter for signal-carrying radio waves for non-contacting transmission of data, mounted at at least one of said apparatus components; and
at least one receiver for signal-carrying radio waves for non-contacting reception of data, mounted at at least one of said holding mechanism and said housing, for continuously exchanging data said first transmitter without contact with said transmitter.

21. An X-ray apparatus as claimed in claim 20 wherein said housing comprises a cart for said C-arm X-ray device.

22. An X-ray apparatus as claimed in claim 20 further comprising a viewing device unit, separate from said C-an X-ray device, comprising a processor for processing data produced by said at least one electrically operating device, and a display device for displaying a result of processing of said data, said processor communicating with said first component to at least receive said data therefrom.

23. An X-ray apparatus comprising:
- a C-arm X-ray device having a C-arm and a holding mechanism, said C-arm being mechanically connected to said holding mechanism for adjustment relative to said holding mechanism;
- a housing at which paid holding mechanism is disposed;
- at feast one electrically operable component mounted at said C-arm, said C-arm and said at least one electrically operable component being apparatus components;
- at least one microwave energy receiver mounted at at least one of said apparatus components; and
- at least one microwave energy transmitter mounted at at least one of said holding mechanism and said housing, for continuously exchanging energy with said microwave energy receiver without contact with said microwave energy receiver.

24. An X-ray apparatus as claimed in claim 23 wherein said microwave energy receiver comprises a component containing a microwave transmission medium connected to said at least one electrically operating component, and wherein said microwave energy transmitter comprises a microwave generator interacting with said component containing said microwave transmission medium.

25. An X-ray apparatus as claimed in claim 24 wherein said microwave transmission medium comprises dipoles.

26. An X-ray apparatus as claimed in claim 24 wherein said microwave transmission medium is water.

27. An X-ray apparatus as claimed in claim 24 wherein said component containing said microwave transmission medium is a plastic tube containing said microwave transmission medium.

28. An X-ray apparatus as claimed in claim 27 wherein said plastic tube contains water as said microwave transmission medium.

29. An X-ray apparatus as claimed in claim 23 wherein said microwave energy receiver comprises a waveguide connected to said at least one electrically operating component, and wherein said microwave energy transmitter comprises a microwave generator which interacts with said waveguide.

30. An X-ray apparatus as claimed in claim 23 wherein said housing comprises a cart for said C-arm X-ray device.

31. An X-ray apparatus as claimed in claim 23 further comprising a viewing device unit, separate from said C-arm X-ray device, comprising a processor for processing data produced by said at least one electrically operating device, and a display device for displaying a result of processing of said data, said processor communicating with said first component to at feast receive said data therefrom.

32. An X-ray apparatus comprising:
- a C-arm X-ray device having a C-arm and a holding mechanism, said C-arm being mechanically connected to said holding mechanism for adjustment relative to said holding mechanism;
- a housing at which said holding mechanism is disposed;
- at least one electrically operable component mounted at said C-arm, said C-arm and said at feast one electrically operable component being apparatus components;
- at least one inductive receiver for non-contacting reception of at least one of data and energy mounted at at least one of said apparatus components; and
- at least one inductive transmitter for at least one of data and energy mounted at at least one of said holding mechanism and said housing, for continuously exchanging at least one of data and energy with said inductive receiver without contact with said inductive receiver.

33. An X-ray apparatus as claimed in claim 32 wherein said inductive receiver has a receiver coil and wherein inductive transmitter has a transmitter coil, said receiver coil and said transmitter coil being inductively coupled for transmission of at least one of data and energy therebetween.

34. An X-ray apparatus as claimed in claim 32 wherein said housing comprises a cart for said C-arm X-ray device.

35. An X-ray apparatus as claimed in claim 32 further comprising a viewing device unit, separate from said C-arm X-ray device, comprising a processor for processing data produced by said at least one electrically operating device, and a display device for displaying a result of processing of said data, said processor communicating with said first component to at least receive said data therefrom.

* * * * *